(12) United States Patent
Dixon et al.

(10) Patent No.: US 7,300,904 B2
(45) Date of Patent: Nov. 27, 2007

(54) TRIMERISATION AND OLIGOMERISATION OF OLEFINS USING A CHROMIUM BASED CATALYST

(75) Inventors: John Thomas Dixon, Vanderbijlpark (ZA); Peter Wasserscheid, Cologne (DE); David Shane McGuinness, Cupar (GB); Fiona Millicent Hess, Vaalpark (ZA); Hulisani Maumela, Johannesburg (ZA); David Hedley Morgan, Johannesburg (ZA); Annette Bollman, Henley-on-Klip (ZA)

(73) Assignee: Sasol Technology (Pty) Ltd., Johannesburg (ZA)

( * ) Notice: Subject to any disclaimer, the term of this patent is extended or adjusted under 35 U.S.C. 154(b) by 0 days.

(21) Appl. No.: 10/499,225

(22) PCT Filed: Dec. 19, 2002

(86) PCT No.: PCT/ZA02/00216

§ 371 (c)(1),
(2), (4) Date: Jan. 26, 2005

(87) PCT Pub. No.: WO03/053890

PCT Pub. Date: Jul. 3, 2003

(65) Prior Publication Data

US 2005/0131262 A1    Jun. 16, 2005

Related U.S. Application Data

(60) Provisional application No. 60/342,560, filed on Dec. 20, 2001.

(30) Foreign Application Priority Data

Dec. 20, 2001  (ZA) ............................... 2001/10435

(51) Int. Cl.
*B01J 31/00* (2006.01)
(52) U.S. Cl. .................. 502/168; 502/102; 502/103; 502/162; 502/167
(58) Field of Classification Search ............ 502/150, 502/168, 162, 167, 102, 103; 585/511; 526/75
See application file for complete search history.

(56) References Cited

U.S. PATENT DOCUMENTS

| | | | |
|---|---|---|---|
| 5,223,631 A * | 6/1993 | Cheng et al. ............... 549/533 |
| 5,621,062 A * | 4/1997 | Castellucci et al. ......... 528/30 |
| 6,337,297 B1 * | 1/2002 | Mimura et al. ............. 502/117 |
| 6,362,309 B1 * | 3/2002 | Lund et al. ................. 528/373 |
| 6,610,805 B1 * | 8/2003 | Guram et al. ............... 526/172 |
| 6,838,563 B2 * | 1/2005 | Mihan et al. ................ 546/10 |
| 6,911,516 B1 * | 6/2005 | Mihan et al. ............... 526/348 |
| 6,924,248 B2 * | 8/2005 | Mihan et al. ............... 502/132 |
| 2003/0149198 A1 | 8/2003 | Small et al. ................ 526/115 |
| 2005/0070425 A1 * | 3/2005 | Biagini et al. ............. 502/117 |

FOREIGN PATENT DOCUMENTS

| | | | |
|---|---|---|---|
| EP | 0537 609 | | 4/1993 |
| JP | 2002241382 A | * | 8/2002 |
| WO | WO 01/83447 | | 11/2001 |
| WO | WO 02/04119 | | 1/2002 |

OTHER PUBLICATIONS

Cooper, T.H. et al., "Kinetic and Thermodynamic Measurements on Branched Amini Polyhiaether Ligands: A Family of Complexing Agents Analogous to EDTA and NTA Exhibiting Enhanced Selectivity for Copper (II)", *Inorganic Chemistry*, vol. 31, pp. 1796-3804, 1992, XP-002237104.
Friebe, M. et al., "Neutral '3+1' Mixed-ligand Oxorhenium (v) Complex with Tridentate [S,N,S] Chelates and Aminoalkanethiols: Synthesis, Characterization and Structure Determination", *Journal of the Chemical Society, Dalton Trans.*, pp. 2471-2475, 2000, XP-002237103.
Konrad, M. et al., "Unsymetrically Substituted Pyrazolates: Nickel (II) Complexes of a Novel Dinucleating Ligand Providing Both N-and S-rich Co-ordination Spheres", *Journal of the Chemical Society, Dalton Trans.*pp. 199-205, 1998, XP-002237101.
Tanaka, M. et al., "Synthesis and Metal-Ion Binding Properties of Monoazathiacrown Ethers", *J. Org. Chem.* vol. 66, pp. 7008-7012, 2001. XP-002237102.
Database Crossfire Beilstein, *Beilstein Institut zur Foerderung der Chemischen Wissenchaffen*, Database accession No. 2441430, XP-002237105, Abstract.
Database Crossfire Beilstein, *Beilstein Institut zur Foerderung der Chemischen Wissenchaffen*, Database accession No. 1978690, XP-002237106, Abstract.

* cited by examiner

*Primary Examiner*—Elizabeth D. Wood
(74) *Attorney, Agent, or Firm*—Occhiuti Rohlicek & Tsao LLP

(57) ABSTRACT

The invention provides a mixed heteroatomic ligand for an oligomerisation of olefins catalyst, which ligand includes at least three heteroatoms, of which at least one heteroatom is sulfur and at least 2 heteroatoms are not the same. The invention also provides a multidentate mixed heteroatomic ligand for an oligomerisation of olefins catalyst, which ligand includes at least three heteroatoms of which at least one is a sulfur atom. The ligand may also contain, in addition to sulfur, at least one nitrogen or phosphorous heteroatom.

13 Claims, 1 Drawing Sheet

US 7,300,904 B2

TRIMERISATION AND OLIGOMERISATION OF OLEFINS USING A CHROMIUM BASED CATALYST

Figure 1:
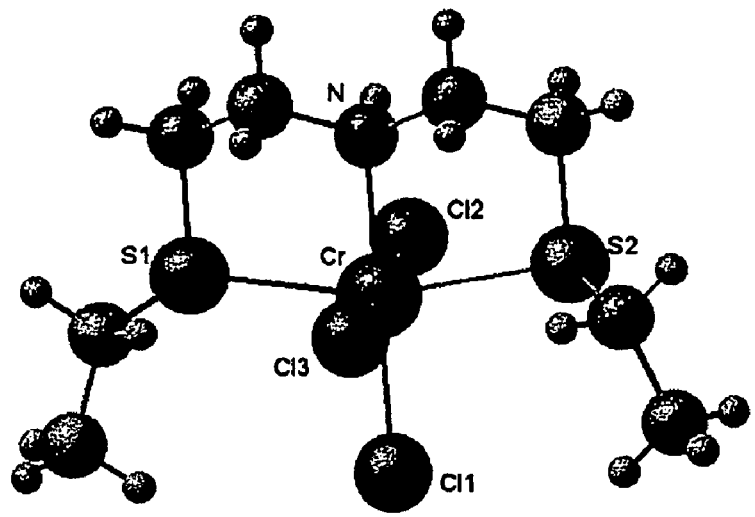

This application is a 371 of PCT/ZA02/00216 filed Dec. 19, 2002 which claims benefit of Ser. No. 60/342,560 filed Dec. 20, 2001.

FIELD OF THE INVENTION

This invention relates to a ligand and a catalyst system, more particularly an olefin oligomerisation or trimerisation catalyst system.

BACKGROUND OF THE INVENTION

The oligomerisation of olefins, primarily α-olefins, with chromium catalysts has been extensively studied. More specifically, a number of chromium catalysts have been developed and used to trimerise olefins. In this regard, the trimerisation of ethylene to 1-hexene is significant since, in addition to its use as a specific chemical, 1-hexene is extensively used in polymerization processes either as a monomer or co-monomer. Furthermore, the trimeric products derived from longer chain olefins could be well utilized as synthetic lubricants (e.g. polyalphaolefins/PAOs), as well as various other applications such as components of drilling muds, and as feedstock to prepare detergents and plasticizers.

Prior art chromium based ethylene trimerisation processes include:

a) A process in which olefins are trimerised by passing the olefin in contact with a catalyst comprising the reaction product of a chromium compound, an organoaluminium compound hydrolyzed with a specific amount of water and a donor ligand selected from hydrocarbyl isonitriles, amines and ethers (U.S. Pat. No. 4,668,838);

b) A process to trimerise ethylene to 1-hexene comprising contacting ethylene with a stabilized catalyst system comprising a chromium source, a pyrrole-containing compound, a metal alkyl and an aromatic compound (European Patent No. 0 668 105);

c) A process for preparing α-olefin oligomers, which comprises carrying out oligomerisation of an α-olefin in a solvent by reacting said α-olefin with a chromium-based catalyst system comprising a combination of at least a chromium compound, an amine or metal amide, and an alkylaluminium compound, in a contacting mode that the chromium compound and the alkylaluminium compound are not previously contacted with each other (U.S. Pat. No. 5,750,817);

d) A process for oligomerising ethylene to produce 1-butene and/or 1-hexene wherein catalytic composition is obtained by mixing at least one chromium compound with at least one aryloxy aluminium compound with general formula $R_nAl(R'O)_{3-n}$ where R is a linear or branched hydrocarbyl radical containing 1 to 30 carbon atoms, R'O is an aryloxy radical containing 6 to 80 carbon atoms and n is a whole which can take the values 0,1 or 2, and with at least one other hydrocarbyl aluminium compound selected from tris(hydocarbyl)aluminium compound or chlorinated or brominated hydrocarbyl aluminium compounds (U.S. Pat. No. 6,031,145); and e) A process for the trimerisation of ethylene, said process comprising reacting ethylene, using a catalyst comprising an aluminoxane and a polydentate phosphine, arsenic and/or antimony coordination complex of a chromium salt, such that 1-hexene is formed (U.S. Pat. No. 5,811,618).

SUMMARY OF THE INVENTION

The invention is now described in general terms with reference to the accompanying drawings.

Figure 2:
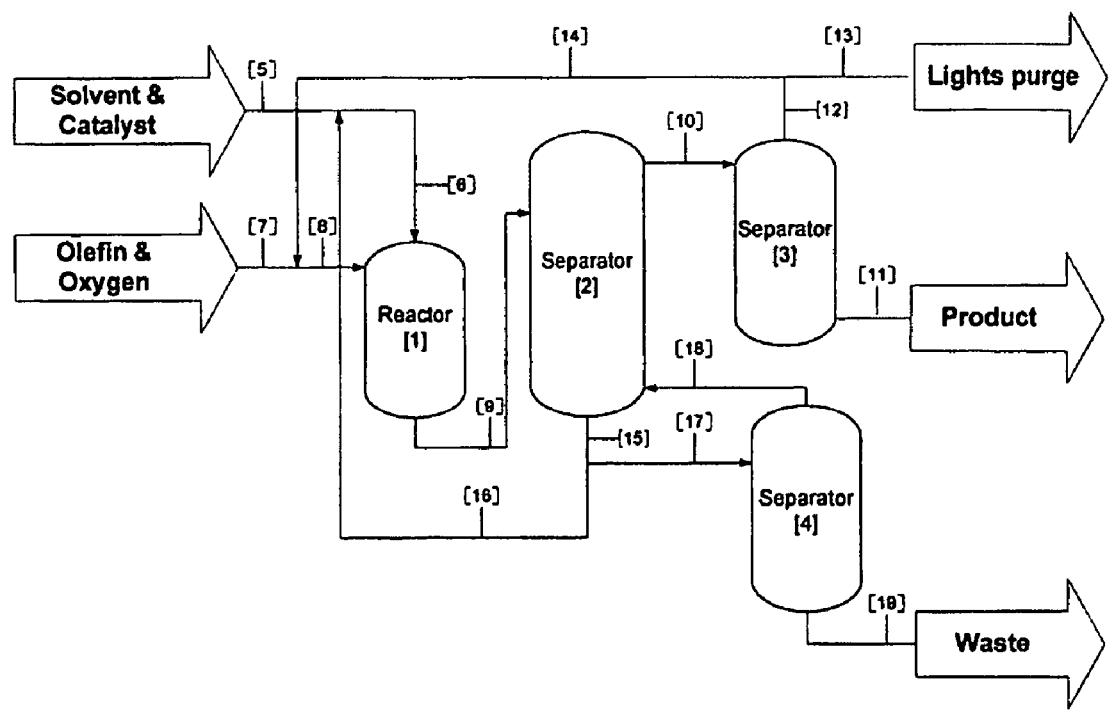

In the drawings:

FIG. 1 shows a X-Ray Crystal structure of $CrCl_3$(bis-(2-ethylsulfanyl-ethyl)-amine), and FIG. 2 shows a schematic representation (flow diagram) of one embodiment of a olefin oligomerisation process, in accordance with the invention.

This invention recognizes the need for a catalyst system, which facilitates the production of 1-hexene in high selectivity while avoiding the co-production of significant quantities of polyethylene. However, the catalyst system can also be used for the trimerisation or oligomerisation of other olefins, especially α-olefins.

In this regard, it is known from the prior art (e.g. European Patent No. 537609) that chromium catalysts comprising a multidentate amine coordination complex of a chromium salt and an aluminoxane or an alkylaluminium compound are generally not particularly effective at trimerising ethylene selectively. This has also been established experimentally as is demonstrated in Example 1 below.

This invention generally relates to how the need for selectively producing 1-hexene from ethylene can be at least partly satisfied by using a chromium catalyst system containing a multidentate ligand with at least one amine functionality.

Thus, according to a first aspect of the invention there is provided a mixed heteroatomic ligand for the oligomerisation of olefins catalyst, which ligand includes at least three donor heteroatoms, of which at least one donor heteroatom is sulfur and at least 2 donor heteroatoms are not the same.

The ligand may be a multidentate mixed heteroatomic ligand which, includes at least three donor heteroatoms of which at least one is a sulfur atom.

The ligand may include, in addition to sulfur, at least one nitrogen or phosphorous donor heteroatom.

The ligand may be selected such that none of the non-carbon based donor heteroatoms are directly bonded to any of the other non-carbon based donor heteroatoms.

By "multidentate mixed heteroatomic" is meant a ligand that contains more than one non-carbon based donor atoms, of which one donor atom is different from the others and of which all the donor atoms are coordinated to the transition metal in the catalyst system. The applicant has found that it is important for catalyst activity that all the non-carbon based donor atoms coordinate with the transition metal, and the ligand therefore preferably, but not necessarily, needs at least one bridging atom between the donor atoms to provide the necessary distances between the donor atoms and to allow the ligand to assume the necessary spatial orientation for coordination of all donor atoms. FIG. 1 contains the molecular structure of a complex between $CrCl_3$ and an example of such a multidentate mixed heteroatomic ligand, namely bis-(2-ethylsulfanyl-ethyl)-amine. Selected bond distances and angles of this molecular structure are summarized in Table 1.

TABLE 1

Selected bond distances and angles of CrCl₃(bis-(2-ethylsulfanyl-ethyl)-amine)

| | |
|---|---|
| Chelate bite angle | 83.07(5)° |
| | 82.90(5)° |
| Cr-S bond distances | 2.4508(7)Å |
| | 2.4556(7)Å |
| Cr-N bond distance | 2.1059(18)Å |

As can be seen from FIG. 1, this specific multidentate mixed heteroatomic ligand has a meridional arrangement in the complex, thereby enabling the formation of two Cr—S bonds with nearly equal bond distances (see Table 1). Such a meridional arrangement of the ligand is only possible if there is at least one bridging atom between the donor atoms. As could be expected, the resulting S—Cr—N chelate bite angles are also very similar in size.

Therefore a multidentate mixed heteroatomic ligand may also be selected such that none of the non-carbon based donor atoms are directly bonded to any of the other non-carbon based donor atoms.

The multidentate mixed heteroatomic ligand may be selected from the following ligand types:

a) $R^1A(R^2BR^3)(R^4CR^5)$ wherein $R^1$, $R^3$ and $R^5$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^4$ may be the same or different and are $C_1$ to about $C_{15}$ hydrocarbyls; A is nitrogen or phosphorous; and B and C are sulfur or selenium; and b) $R^1A(R^2BR^3R^4)(R^5CR^6)$ wherein $R^1$, $R^3$, $R^4$, and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^5$ may be the same or different and are $C_1$ to about $C_{15}$ hydrocarbyls; A and B are individually nitrogen or phosphorous; and C is sulfur; and c) $A(R^1BR^2R^3)(R^4CR^5)$ wherein $R^2$, $R^3$, and $R^5$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B is nitrogen or phosphorous; and A and C are sulfur; and d) $A(R^1BR^2R^3)(R^4CR^5R^6)$ wherein $R^2$, $R^3$, $R^5$ and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B and C are individually nitrogen or phosphorous; and A is sulfur.

These multidentate mixed heteroatom based ligands can be synthesized according to procedures described in the literature, for example by A. Heβler et al., *J. Organomet. Chem*, 1998, 533, 39-52, M. Tanaka et al. *J. Org. Chem.*, 2001, 66, 7008-7012, M. Konrad, F. Meyer, K. Heinze, L. Zsolnai. *J. Chem. Soc., Dalton Trans.*, 1998 199-205 and G. Gelbard and P. Rumpf, *Bull. Soc. Chem.*, 1969, 1161-1170.

Specific examples of multidentate mixed heteroatom based ligands may include bis-(2-ethylsulfanyl-ethyl)-amine, bis-(2-methylsulfanyl-ethyl)-amine, bis-(2-butylsulfanyl-ethyl)-amine, bis-(2-decylsulfanyl-ethyl)-amine, bis-(ethylsulfanyl-methyl)-amine, bis-(2-ethylsulfanyl-phenyl)-amine, bis-(2-ethylsulfanyl-ethyl)-phosphine, bis-(2-ethylsulfanyl-ethyl)-ethylphosphine, bis-(2-ethylsulfanyl-ethyl)-phenylphosphine, N-methylbis-(2-ethylsulfanyl-ethyl)-amine, (2-ethylsulfanyl-ethyl)(3-ethylsulfanyl-propyl)-amine, (2-ethylsulfanyl-ethyl)(2-diethylphosphino-ethyl)-amine, (2-ethylsulfanyl-ethyl)(2-diethylphosphino-ethyl)-sulfide, (2-ethylsulfanyl-ethyl)(2-diethylamino-ethyl)-amine, (2-ethylsulfanyl-ethyl)(2-diethylamino-ethyl)-sulfide, (2-ethylsulfanyl-ethyl)(2-diethylphosphino-ethyl)-ethylphosphine, (2-ethylsulfanyl-ethyl)(2-diethylphosphino-ethyl)-phosphine, (2-ethylsulfanyl-ethyl) (2-diethylamino-ethyl)-ethylphosphine, (2-ethylsulfanyl-ethyl)(2-diethylamino-ethyl)-phosphine, bis-(2-diethylphosphino-ethyl)-sulfide, bis-(2-diethylamino-ethyl)-sulfide and (2-diethylphosphino-ethyl)(2-diethylamino-ethyl)-sulfide.

Suitable multidentate mixed heteroatomic ligands are bis-(2-ethylsulfanyl-ethyl)-amine and bis-(2-decylsulfanyl-ethyl)-amine and derivatives thereof.

The multidentate mixed heteroatomic ligands can be modified to be attached to a polymer chain (molecular wt.=1000 or higher) so that the resulting transition metal complex is soluble at elevated temperatures, but becomes insoluble at 25° C. This approach would enable the recovery of the complex from the reaction mixture for reuse and has been used for other catalyst as described by D. E. Bergbreiter et al., *J. Am. Chem. Soc.*, 1987, 109, 177-179. In a similar vain these transition metal complexes can also be immobilized by bounding the multidentate mixed heteroatomic ligands to silica, silica gel, polysiloxane or alumina backbone as demonstrated by C. Yuanyin et al., *Chinese J. React. Pol.*, 1992, 1(2), 152-159 for immobilizing platinum complexes.

According to a further aspect of the invention, there is provided an oligomerisation of olefins catalyst system, which includes a mixed heteroatomic ligand, as described above.

The term "oligomerisation" generally refers to a reaction were all the monomer units of the oligomerisation product are the same. However, it may also include co-oligomerisation reactions where mixtures of olefins are used as the reagents thereby yielding products containing more than one type of monomer unit (i.e. different olefins). Such co-oligomerisation reactions often yield alkyl- and/or aryl-branched oligomeric products with distinct properties as demonstrated by C. Pelecchia et al., *Macromolecules*, 2000, 33, 2807-2814.

The catalyst system may include a transition metal.

The transition metal may be chromium. Molybdenum, tungsten, titanium, nickel, and tantalum may also be used.

The catalyst system may include a combination of a mixed heteroatomic coordination complex of chromium and an aluminoxane.

The chromium coordination complexes which, upon mixing with an aluminoxane, catalyze ethylene trimerisation in accordance with the invention, may be suitably expressed by the formula $LCrX_n$ wherein X represents anions which can be the same or different, n is an integer from 0 to 5 and L is a mixed heteroatomic ligand.

The chromium precursor used in the preparation of the coordination complex may be selected from an organic or inorganic chromium compound, with the oxidation state of the chromium atom ranging from 0 to 6.

Chromium salts used in the preparation of the chromium coordination complex may be selected from chromium(III) acetylacetonate, chromium (III) acetate, chromium (III) 2,2,6,6-tetramethylheptadionate, chromium (III) tris(2-ethylhexanoate, chromium (III) chloride, chromium (II) acetate, chromium (II) chloride, chromium (II) nitrate and chromium (III) sulphate.

Alternatively, organometallic complexes, for example, chromium trichloride tris-tetrahydrofuran complex, (benzene)tricarbonyl chromium, chromium hexacarbonyl, and the like, may be used in the preparation of the chromium coordination complex.

Aluminoxanes for use in the catalyst system can be prepared as known in the art by reacting water or water containing materials with trialkylaluminium compounds. Preferred aluminoxanes are prepared from trialkylaluminium compounds such as trimethylaluminium, triethylaluminium, tripropylaluminium, tributylaluminium, triisobutylaluminium, thrihexylaluminium or the like, and mixtures thereof. Mixtures of different aluminoxanes may also be used in the catalyst system. Of these, the more preferred aluminoxane is prepared from trimethylaluminium and/or triethylaluminium. The use of said aluminoxane is necessary to achieve catalytic activity.

The catalyst system may include, in addition to the aluminoxane or mixture of aluminoxanes, also a trialkylaluminium in amounts of between 0.01 to 100 mole per mole of aluminoxane. It should however be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The applicant has found that the trialylaluminium serves as a poisons scavenger to protect the aluminoxane and in some cases leads to an increase in the catalytic activity.

The aluminoxane may form part of a mixture of aluminoxanes. The applicant has found that at least a portion of the required more expensive methylaluminoxane can be replaced with a less expensive ethylaluminoxane, for example, and the resulting mixture shows the same, if not increased, catalytic activity.

The aluminoxane or mixture of aluminoxanes may preferably be selected from methylaluminoxane or ethylaluminoxane.

The chromium coordination complex and the aluminoxane may be combined in proportions to provide Al/Cr molar ratios of from about 1:1 to 10 000:1.

The hydrocarbon conversion catalyst system may be a trimerisation of α-olefins or trimerisation of ethylene catalyst system.

The hydrocarbon conversion catalyst system described in this invention may also be used in combination with another catalyst system suitable for the polymerization of olefins. In such cases, the oligomerization or trimerisation products of the catalyst system disclosed in this invention could be incorporated into a polymer or other chemical product with desired properties. This concept of using dual catalyst systems, one for oligomerization and the other for polymerization of olefins, to manufacture polyethylene copolymers has been demonstrated before for example by G. C. Bazan, Z. J. A. Komon and X. Bu, *J. Am. Chem. Soc.*, 2000, 122, 1830 and C. Pelecchia et al., *Macromolecules*, 2000, 33, 2807-2814.

The catalyst system may be a trimerisation of α-olefins or trimerisation of ethylene catalyst system.

The multidentate mixed heteroatomic coordination complex of a chromium salt may be either added to the reaction mixture, or generated in-situ. Known literature procedures can be used for the ex-situ preparation of such coordination complexes of a chromium salt. Examples of such procedures are described by R. D Köhn and G. K. Köhn, *Angew. Chem. Int. Ed. Engl.*, 1994, 33(18), 1877-1878, R. D Köhn et al., *Angew. Chem. Int. Ed.*, 2000, 39(23), 43374339 and P. Wasserscheid et al., *Adv. Synth. Catal.*, 2001, 343(8), 814-818.

The catalyst system may include an inert solvent. These inert solvents include any saturated aliphatic and unsaturated aliphatic and aromatic hydrocarbon and halogenated hydrocarbon. The saturated aliphatic and unsaturated aliphatic hydrocarbon compound can have any number of carbon atoms per molecule, but usually contain less than 20 carbon atoms due to commercial availability and end use. Preferred solvents include, but are not limited to, benzene, toluene, xylene, ethylbenzene, mesitylene, heptane, nonane, cyclohexane, methylcyclohexane, 1-hexene, chlorobenzene, anisole and the like.

The individual components of the catalyst system described in this disclosure may be combined simultaneously or sequentially in any order, and in the presence or absence of a solvent, in order to give an active catalyst. The mixing of the catalyst components can be conducted at any temperature between 0° C. and 150° C. The temperature during the mixing of the catalyst components does not seem to have a significant effect on the catalyst performance. The presence of an olefin during the mixing of the catalyst components generally provides a protective effect which may result in improved catalyst performance.

The chromium coordination complex and the aluminoxane are combined in proportions to provide Al/Cr molar ratios of from about 1:1 to 10 000:1, and preferably, from about 1:1 to 1000:1. In this respect, it was found that generally significant lower Al/Cr molar ratios are required to achieve an acceptable catalyst performance when the chromium coordination complex is completely soluble in the solvent employed for the oligomerisation reaction.

The catalyst system, or its individual components, may also be immobilized by supporting it on a heterogeneous surface such as silica, alumina, silica-alumina, MgO, zirconia or the like. This approach would also facilitate the recovery of the catalyst from the reaction mixture for reuse. The concept was successfully demonstrated with another chromium-based ethylene trimerisation catalyst by T. Monoi and Y. Sasaki, *J. Mol. CatA:Chem.*, 1987, 109, 177-179. In some cases, the heterogeneous surface (support) can also act as a catalyst component, for example where such supports contain aluminoxane functionalities or where the support is capable of performing similar chemical functions as an aluminoxane, which is for instance the case with IOLA™ (a commercial product from Davison Catalysts).

It was thus found that the hydrocarbon conversion catalyst system described in this invention suffered nearly no detectable decrease in its catalytic performance when alumina supported aluminoxane is used, instead of unsupported aluminoxane, during the preparation of the catalyst system.

According to a further aspect there is provided a process for the oligomerisation of olefins, the process including the step of contacting the olefins at pressures from atmospheric to 100 barg and at temperatures of from 0° C. to 200° C., with a catalyst system as described above.

The process of this invention may also be carried out in an inert solvent. Any inert solvent that does not react with trialkylaluminium and aluminoxane compounds can be used. These inert solvents include any saturated aliphatic and unsaturated aliphatic and aromatic hydrocarbon and halogenated hydrocarbon. Preferred solvents include, but are not limited to, benzene, toluene, xylene, heptane, cyclohexane, 1-hexene and the like. The amount of solvent is not exceptionally critical and generally ranges from about 50 to 99.9 wt % of the initial reaction mixture. Nevertheless, since the catalyst productivity tends to be somewhat higher at fairly low catalyst concentrations in the initial reaction mixture (typically in the range of 0.001-0.1 mmol Cr/100 ml reaction mixture), the catalyst concentration is chosen such that the catalyst productivity and selectivity is maximized.

The catalyst is dissolved in an inert solvent.

The process may include the step of generating the multidentate mixed heteroatomic complex of a chromium salt in-situ in a reaction mixture.

The process of this invention may be carried at pressures from atmospheric to 100 barg. Generally the process can be performed at any pressure within this range, but here again the actual reaction pressure is chosen such that the catalyst productivity and selectivity is maximized. Ethylene pressures in the range of 30-60 bar are particularly preferred.

The process of this invention may be carried out at temperatures from 0° C. to 200° C. The process can normally be conducted at any temperature within this range, but as is the case with the ethylene pressure, the actual reaction temperature is chosen such that the catalyst productivity and selectivity is maximized. Temperatures in the range of 80-120° C. are particularly preferred.

The process may be carried out in the presence of an oxidizing agent such as oxygen or the like.

The process can normally be conducted at any temperature within this range, but as is the case with the ethylene pressure, the actual reaction temperature is chosen such that the catalyst productivity and selectivity is maximized. Temperatures in the range of 80-120° C. are particularly preferred.

The process may be carried out in the presence of an oxidizing agent such as oxygen or the like. In this respect it was found that the use of olefin reagents, such as ethylene, containing low quantities of oxygen (1-2000 parts per million) resulted in improvements in the performance of the catalyst system as well as in the product selectivity.

Although the catalyst, its individual components, reagents, solvents and reaction products are generally employed on a once-through basis, any of these materials can, and are indeed preferred to, be recycled to some extent in order to minimize production costs.

This process may comprise, in combination a) a reactor, b) at least one inlet line into this reactor for olefin reactant and the catalyst system, c) effluent lines from this reactor for oligomerisation reaction products, and d) at least one separator to separate the desired oligomerisation reaction products, wherein the catalyst system may include a multidentate mixed heteroatomic coordination complex of a chromium salt and an aluminoxane.

FIG. 2 is a schematic representation (flow diagram) of one embodiment of this olefin oligomerisation process using three separators to separate the reaction products, solvent and spent catalyst (waste). While this drawing describes one embodiment of the invention for the purpose of illustration, the invention is not to be construed as limited by this schematic flow diagram, but the drawing is rather intended to cover all changes and modifications within the spirit and scope thereof.

Various additional pumps, valves, heaters, coolers and other conventional equipment necessary for the practice of this invention will be familiar to one skilled in the art. These additional equipment have been omitted from FIG. 2 for the sake of clarity.

The following description of the flow diagram shown in FIG. 2 provides one method of operating the process, in accordance with the invention, and aims to give a further understanding of the aspects of this invention. As used in the description, "reactor effluent" refers to all components that can be removed from an oligomerisation reactor, including, but not limited to, unreacted olefin, catalyst system, oligomerisation product(s) and co-product(s). "Waste" refers to reaction co-product(s) with a higher molecular mass than the desired oligomerisation reaction product, polymeric products and the used catalyst system. "Product" refers to product(s) of the olefin oligomerisation reaction.

Olefin, and optionally oxygen or air, is fed trough inlet line 7/8 into the oligomerisation reactor 1. Inlet line 5/6 introduces the catalyst system and optionally, solvent, into the oligomerisation reactor 1. Reactor effluent is removed from reactor 1 via line 9. It should be noted that lines 6, 8 and 9 can be located is anywhere on the reactor 1. It is preferable that the contents in lines 9, 15, 16, 17 and 19 is maintained at a higher temperature in order to keep undesirable polymer particles from precipitating. The formation of such particles may have a detrimental effect on the operation of this process.

Line 9 introduces reactor effluent into separator 2 that separates unreacted olefin and reaction product(s) from higher boiling solvent(s), reaction product(s) and the used catalyst system. Lines 15/16 is an optional embodiment of the invention and can be used to facilitate the return of the higher boiling compounds in the reactor effluent, including the catalyst system, to reactor 1 via inlet line 6. Line 15/17 transports an effluent stream, comprising higher boiling compounds and used catalyst system, from separator 2 to separator 4, which separates the solvent from all other compounds in this effluent stream. Line 18 is used to return the solvent to separator 2. Line 19 is an effluent line that transports waste from separator 4. Line 10 transports effluent comprising unreacted olefin and the major reaction product(s) from separator 2 to separator 3, that separates the unreacted olefin from the major reaction product(s).

Line 12/14 contains effluent comprising unreacted olefin and small quantities of very light boiling reaction product(s), e.g. 1-butene, and facilitates the recovery of the olefinic reagent by transporting it back to inlet line 6. Line 12/14 is a purge line containing unreacted olefin and small quantities of very light boiling reaction product(s) that is used to prevent a build up of very light boiling reaction product(s). Line 11 is an effluent line containing the major reaction product(s).

In another embodiment of the process the reactor and a separator may be combined to facilitate the simultaneous formation of reaction products and separation of these compounds from the reactor. This process principle is commonly known as reactive distillation when the reaction is a homogeneous liquid phase reaction. When the catalyst system exhibits no solubility in the solvent or reaction products, and is fixed in the reactor so that it does not exit the reactor with the reactor product, solvent and unreacted olefin, the process principle is commonly known as catalytic distillation.

The oligomerisation process described herein may be used in a process in which trimerisation and polymerization of ethylene occur simultaneously leading to the incorporation of the trimerisation products into a copolymer. One example of this type of process is described in U.S. Pat. No. 5,786,431.

EXAMPLES OF PERFORMING THE INVENTION

The invention will now be described with reference to the following examples which are not in any way intended to limit the scope of the invention.

In the examples that follow all procedures were carried out under inert conditions, using pre-dried reagents. Chemicals were obtained from Sigma-Aldrich Company unless stated otherwise. All trialkylaluminium and aluminoxane compounds and solutions thereof were obtained from Crompton and Albemarle Corporation. In all the examples, the molar mass of methylaluminoxane (MAO) was taken to be 58.016 g/mol, corresponding to the ($CH_3$—Al—O) unit, in order to calculate the molar quantities of MAO used in the preparation of the catalyst systems described in the examples below. Similarly the molar mass of ethylaluminoxane (EAO) was taken as 72.042 g/mol, corresponding to the ($CH_3CH_2$—Al—O) building block. Ethylene oligomerisation reaction products were analyzed by GC-MS and GC-FID.

Example 1

Reaction of $CrCl_3$(pentamethyldiethylenetriamine)/MAO with Ethylene

The reaction was conducted in a 75 mL stainless steel autoclave equipped with an addition funnel, gas inlet valve and a magnetic stirrer bar. The addition funnel was charged with 0.0149 g (0.0449 mmol) of $CrCl_3$(pentamethyldietylenetriamine) dissolved in 20 mL of toluene and to the base of the autoclave was added 9.0 mL of 1.5M MAO solution in toluene. Over 20 minutes the base of the autoclave was heated to 100° C., after which time the reactor was charged with ethylene to a pressure of 40 bar and the addition funnel was opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by gas-chromatography (GC). The liquid contained in the autoclave was quenched with ethanol followed by 10% hydrochloric acid, and nonane was added as a GC internal standard. The liquid/internal standard mixture was also analysed by GC. Both GC analyses indicated that 0.12 g oligomers were formed of which 0.0048 g (4 mass %) were hexene isomers. Filtration of the liquids gave 0.12 g of polyethylene.

Example 2

Preparation of (bis-(2-ethylsulfanyl-ethyl)-amine)

A solution of NaOH (6.0 g, 150 mmol) and ethanethiol (9.3 g, 150.0 mmol) in ethanol (150 ml) was added to a solution of bis(2-chloroethyl)amine hydrochloride (8.8 g, 50.0 mmol) in ethanol (100 ml) at 0° C. The solution was stirred for 2 hours at 0° C., then overnight at r.t. After filtering, the filtrate was evaporated to dryness. The residue was taken up in 40-ml diethyl ether and filtered again. After evaporation of the solvent in vacuo, the product remained as a colourless semisolid. Yield: 5.39 g (56%). $^1$H-NMR (CDCl$_3$) δ 1.20 (6H, t, $CH_3$), 2.52 (1H, s, NH), 2.57 (4H, q, $SCH_2CH_3$), 2.70 (4H, t, $SCH_2$), 2.83 (4H, t, $NCH_2$).

Example 3

Preparation of (bis-(2-decylsulfanyl-ethyl)-amine)

A solution of NaOH (3 g, 75 mmol) and decanethiol (15.5 ml, 75 mmol) in ethanol (75 ml) was added to a solution of bis(2-chloroethyl)amine hydrochloride (4.4 g, 25 mmol) in ethanol (50 ml) at 0° C. The solution was stirred for 2 hours at 0° C. and then for another 16 h at room temperature. After filtering, the filtrate was evaporated to dryness. The residue was taken up with dry ether and filtered again. After evaporation of the solvent under vacuum, the product remained as a colourless semi-solid. Yield: 9.4 g (90%). $^1$H-NMR (CDCl$_3$) δ 0.87 (6H, t, $CH_3$), 1.25-1.4 (28H, m, $SC_2H_4C_7H_{14}CH_3$), 1.56 (4H, qn, $SCH_2CH_2C_8H_{17}$), 1.88 (1H, s, NH), 2.52 (4H, qt, $SHCH_2C_9H_{19}$), 2.69 (4H, t, $SCH_2CH_2NH$), 2.82 (4H, t, $NCH_2$).

Example 4

Preparation of $CrCl_3$(bis-(2-ethylsulfanyl-ethyl)-amine)

A solution of bis[2-(ethylsulfanyl)ethyl]amine (1.06 g, 5.5 mmol) in 20 ml THF was added to a solution of 1.87 g (5 mmol) $CrCl_3(THF)_3$ in 50 ml THF at room temperature. The solution turned blue-green immediately and was stirred for 10 min, after which the solvent was removed in vacuo until about 25 ml remained. A further 50-ml of diethyl ether was added, the solution was filtered and the solid washed, first with a mixture of diethyl ether and THF (50 ml each), then with a further 50 ml of diethyl ether. The solid was dried in vacuo. Yield: 1.28 g (72.6%). Elemental analysis: Calculated for $C_8H_{19}S_2NCl_3Cr$ (found): C 27.32 (26.97), H 5.45 (5.99), N 3.98 (3.64). Crystal data: monoclinic space group P2$_1$/c, a=7.6255(12), b=13.059(5), c=14.3703(10) Å, β=90.790(11)°, V=1430.9(6) Å$^3$, Z=4, D$_c$=1.633 g·cm$^{-3}$, μ=1.622 mm$^{-1}$, F(000)=724, 2θ$_{max}$=54°, 4013 reflections, 3126 independent data. Convergence for 138 parameters at wR2=0.0857, R1=0.0351, GOF=1.074 for all data and R1=0.0309 for 2846 reflections with I>2(I). Residual electron density was 0.439 and −0.549 e·Å$^3$. Selected bond distances (Å) and angles (°): Cr—N 2.1059(18), Cr—S1 2.4508(7), Cr—S2 2.4556(7), Cr—Cl1 2.2985(8), Cr—Cl2 2.3184(7), Cr—Cl3 2.3167(7), N—Cr—S1 83.07(5), N—Cr—S2 82.90(5), S1-Cr—Cl1 97.20(2), S2-Cr—Cl1 96.85(2), N—Cr—Cl1 179.71(5), N—Cr—Cl2 85.82(6) and N—Cr—Cl3 88.64(6).

Example 5

Preparation of $CrCl_3$(bis-(2-decylsulfanyl-ethyl)-amine)

A solution of 3.93 g (9.4 mmol) of (bis-(2-decylsulfanyl-ethyl)-amine) in 80 ml THF was added to a solution of 3.21 g (8.6 mmol) $CrCl_3(THF)_3$ in 50 ml THF at room temperature. The solution turned blue-green immediately and was stirred for 10 min after which all the solvent was removed in vacuo. Diethylether (80 ml) was added to the residue and the solution was cooled overnight in a refrigerator. The solution was then filtered and the solid was washed with diethyl ether (3×60 ml). The solid was dried in vacuo. Yield: 3.68 g (74.3%). Elemental analysis: Calculated for $C_{24}H_{51}S_2NCl_3Cr$ (found): C 50.04 (50.23), H 8.86 (9.19), N 2.43. (2.16).

Example 6

Ethylene Trimerisation Reaction Using $CrCl_3$(bis-(2-ethylsulfanyl-ethyl)-amine)/MAO $CrCl_3$(bis-(2-ethylsulfanyl-ethyl)-amine) (0.01407 g, 0.04 mmol) was combined with 20 ml toluene in a Schlenk vessel and stirred for 5 minutes at room temperature. The resulting suspension was then transferred to a 300 ml pressure reactor (autoclave) containing a mixture of toluene (80 ml) and MAO (methylaluminoxane, 27.2 mmol) at 90° C. The pressure reactor was charged with ethylene after which the reactor temperature was maintained at 100° C., while the ethylene pressure was kept at 40 barg. Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID and GC-MS. The remainder of the organic layer was filtered to isolate the solid polymeric products. These solid products were dried overnight in an oven at 100° C. and then weighed to yield 0.47 g of dry polymer. The GC analyses indicated that the reaction mixture contained 46.85.g oligomers. The product distribution of this example is summarized in Table 2.

Example 7-19

Ethylene Trimerisation Reaction Using $CrCl_3$(bis-(2-ethylsulfanyl-ethyl)-amine)/MAO Examples 7 to 19 were carried out using the procedure of Example 6 above with variations in the reaction conditions, quantities of $CrCl_3$(bis-(2-ethylsulfanyl-ethyl)-amine) and MAO employed and the type of solvent used. The total volume of the reaction mixture at the start of each reaction was 100 ml throughout. The results obtained for these examples are summarized in Table 2.

Example 20

Ethylene Trimerisation Reaction Using $CrCl_3$(bis-(2-decylsulfanyl-ethyl)-amine)/MAO A 0.004 molar solution of $CrCl_3$(bis-(2-decylsulfanyl-ethyl)-amine) in toluene (6 ml, 0.024 mmol) was transferred to a 300 ml pressure reactor (autoclave) containing a mixture of toluene (94 ml) and a MAO (methylaluminoxane, 1.12 mmol) at 80° C. The pressure reactor was charged with ethylene after which the reactor temperature was maintained at 90° C., while the ethylene pressure was kept at 30 barg. Thorough mixing was ensured throughout by mixing speeds of 1100 RPM using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.09 g of dry polymer. The GC analyses indicated that the reaction mixture contained 43.90.g oligomers. The product distribution of this example is summarized in Table 3.

Example 21-27

Ethylene Trimerisation Reaction Using $CrCl_3$(bis-(2-decylsulfanyl-ethyl)-amine)/MAO Examples 21 to 27 were carried out using the procedure of Example 6 above with variations in the reaction conditions and the quantities of $CrCl_3$(bis-(2-ethylsulfanyl-ethyl)-amine) and MAO employed. The total volume of the reaction mixture at the start of each reaction was 100 ml throughout. The results obtained for these examples are summarized in Table 3.

Example 28

Preparation of MAO on Alumina

Alumina (obtained from Sasol Chemie Gmbh as Puralox SBa200) was calcined for 3 hours at 550° C. under a nitrogen flow. The calcined alumina (4.80 g) was suspended in toluene (20 ml). MAO/toluene solution (1.068M, 14.53 mmol, 13.6 ml) was added slowly via a syringe to this alumina/toluene slurry and the resulting mixture was stirred for 2 hours at room temperature. The supernatant solvent was finally taken off with a syringe.

Ethylene Trimerisation Reaction Using $CrCl_3$(bis-(2-decylsulfanyl-ethyl)-amine)/alumina Supported MAO A 0.001097 molar solution of $CrCl_3$(bis-(2-decylsulfanyl-ethyl)-amine) in toluene (21.88 ml, 0.024 mmol) was added to the alumina supported MAO (14.53 mmol on 4.80 g support). The resulting suspension was stirred at room temperature for 5 minutes whereafter it was transferred to a 300 ml pressure reactor (autoclave) containing toluene (78.1 ml) at 75° C. The pressure reactor was charged with ethylene after which the reactor temperature was maintained at 90° C., while the ethylene pressure was kept at 30 barg. Thorough mixing was ensured throughout by mixing speeds of 1100 RPM using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard for the analysis of the liquid phase by GC-FID. The two phases of the reaction mixture were separated and the liquid phase was analysed directly by GC-FID. The solid particles in the reaction mixture was first exposed to air before being dried overnight in an oven at 100° C. and then weighed. The mass of the dried solids was 5.48 g, indicating the formation of 0.65 g polymer during the reaction. The GC analyses indicated that the reaction mixture contained 40.99 g oligomers, of which 0.4 mass % were butene isomers, 97.7 mass % were hexene isomers (99.6% being 1-hexene), 0.3 mass % were octene isomers and 0.5 mass % were decene isomers and heavier products.

Example 29

Ethylene Trimerisation Reaction Using $CrCl_3$(bis-(2-ethylsulfanyl-ethyl)-amine)/MAO or Used MAO A 300 ml pressure vessel was connected to a vacuum pump via a stainless steel tube with two glass cold traps, a pressure gauge and a needle valve (to seal the reactor off) between the vacuum pump and the reactor.

The following five steps were followed:

1) $CrCl_3$(bis-(2-ethylsulfanyl-ethyl)-amine) (0.01055g, 0.03 mmol) was combined with 20 ml toluene in a Schlenk vessel and stirred for 5 minutes at room temperature. The resulting suspension was then transferred to the pressure reactor containing a mixture of toluene (80 ml) and a MAO (methylaluminoxane, 9.0 mmol) at 85° C. The pressure reactor was charged with ethylene after which the reactor temperature was maintained at 90° C., while the ethylene pressure was kept at 30 barg. Thorough mixing was ensured throughout by mixing speeds of 1100 RPM using a gas entraining stirrer.

2) After 30 minutes, the temperature was decreased to 20° C. and the stirring rate to 300 rpm, whereafter the excess ethylene was released slowly, taking care to introduce a nitrogen blanket into the reactor once the pressure had dropped below 1 barg. Once fully depressurized, the reactor was sealed off and the needle valve leading to the cold traps and the vacuum pump was opened gradually until the pressure inside the reactor had decreased to 100 millibar under atmospheric pressure. At this point, the temperature of reaction mixture was also increased to 90° C. and a distillate formed which was collected in the cold traps. As soon as the formation of the distillate ceased, the needle valve outlet to vacuum system was closed and the contents of the reactor was placed under a nitrogen blanket again. The estimated loss of toluene from the reactor during this flash distillation step was 33 ml.

3) New $CrCl_3$(bis-(2-ethylsulfanyl-ethyl)-amine) (0.01055 g, 0.03 mmol) was then added to the reactor as a suspension in toluene, but in 33 ml toluene (instead of the initial 20 ml) to ensure that the quantity of toluene in the reactor remains more or less constant at 100 ml. The pressure reactor was charged again with ethylene while the reactor temperature was maintained at 90° C. and the ethylene pressure kept at 30 barg. The mixing speed was also increased again to 1100 RPM.

4) Steps 2 and 3 were repeated another two times before moving onto step 5.

5) The reaction was terminated after 30 minutes by discontinuing the ethylene feed to the reactor and cooling the reactor to below 10° C. After releasing the excess ethylene from the autoclave, the contents of the reactor was combined with the contents of the cold traps and either nonane was added as an internal standard for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.70 g of dry polymer. The GC analyses indicated that liquid phase contained 161.64 g oligomers, of which 97.9 mass % were hexene isomers (99.5% being 1-hexene).

Example 30

Ethylene Trimerisation Reaction Using $CrCl_3$(bis-(2-decylsulfanyl-ethyl)-amine)/EAO A 0.004 molar solution of $CrCl_3$(bis-(2-decylsulfanyl-ethyl)-amine) in toluene (7.5 ml, 0.03 mmol) was transferred to a 300 ml pressure reactor (autoclave) containing a mixture of toluene (92.5 ml) and EAO (ethylaluminoxane, 30.0 mmol) at 80° C. The pressure reactor was charged with ethylene after which the reactor temperature was maintained at 90° C., while the ethylene pressure was kept at 30 barg. Thorough mixing was ensured throughout by mixing speeds of 1200 RPM using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 2.37 g of dry polymer. The GC analyses indicated that the reaction mixture contained 9.52 g oligomers, of which 3.4 mass % were butene isomers, 85.5 mass % were hexene isomers (98.2% being 1-hexene), 0.8 mass % were octene isomers and 10.1 mass % were decene isomers and heavier products.

Example 31

Ethylene Trimerisation Reaction Using $CrCl_3$(bis-(2-decylsulfanyl-ethyl)-amine)/EAO/TMA A 0.004 molar solution of $CrCl_3$(bis-(2-decylsulfanyl-ethyl)-amine) in toluene (7.5 ml, 0.03 mmol) was transferred to a 300 ml pressure reactor (autoclave) containing a mixture of toluene (92.5 ml), EAO (ethylaluminoxane, 30.0 mmol) and TMA (trimethylaluminium, 3.0 mmol) at 80° C. The pressure reactor was charged with ethylene after which the reactor temperature was maintained at 90° C., while the ethylene pressure was kept at 30 barg. Thorough mixing was ensured throughout by mixing speeds of 1200 RPM using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard,for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.20 g of dry polymer. The GC analyses indicated that the reaction mixture contained 23.90 g oligomers, of which 1.5 mass % were butene isomers, 96.1 mass % were hexene isomers (98.9% being 1-hexene), 0.6 mass % were octene isomers and 1.7 mass % were decene isomers and heavier products.

Example 32

Ethylene Trimerisation Reaction Using CrCl$_3$(bis-(2-decylsulfanyl-ethyl)-amine)/EAO/MAO A 0.004 molar solution of CrCl$_3$(bis-(2-decylsulfanyl-ethyl)-amine) in toluene (7.5 ml, 0.03 mmol) was transferred to a 300 ml pressure reactor (autoclave) containing a mixture of toluene (92.5 ml), EAO (ethylaluminoxane, 8.55 mmol) and MAO (methylaluminoxane, 0.45 mmol) at 80° C. The pressure reactor was charged with ethylene after which the reactor temperature was maintained at 90° C., while the ethylene pressure was kept at 30 barg. Thorough mixing was ensured throughout by mixing speeds of 1200 RPM using a gas entraining stirrer. The reaction was terminated after 30 minutes by discontinuing the ethylene feed to the reactor and cooling the reactor to below 10° C. After releasing the excess ethylene from the autoclave, nonane or heptane was added as an internal standard for the analysis of the liquid phase by GC-FID. The liquid contained in the autoclave was quenched with ethanol followed by 10% hydrochloric acid in water. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.95 g of dry polymer. The GC analyses indicated that the reaction mixture contained 53.66 g oligomers, of which 0.2 mass % were butene isomers, 96.6 mass % were hexene isomers (99.5% being 1-hexene), 0.4 mass % were octene isomers and 2.7 mass % were decene isomers and heavier products.

Example 33

Ethylene Trimerisation Reaction Using CrCl$_3$(bis-(2-methylsulfanyl-ethyl)-amine)/MAO The reaction was conducted in a 75 mL stainless steel autoclave equipped with an addition funnel, gas inlet valve and a magnetic stirrer bar. The addition funnel was charged with 0.0039 g (0.012 mmol) of CrCl$_3$(bis-(2-methylsulfanyl-ethyl)-amine) dissolved in 20 mL of toluene and to the base of the autoclave was added 4.8 mL of 1.5M MAO solution in toluene. Over 20 minutes the base of the autoclave was heated to 80° C., after which time the reactor was charged with ethylene to a pressure of 40 bar and the addition funnel was opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by GC. The liquid contained in the autoclave was quenched with ethanol followed by 10% hydrochloric acid, and nonane was added as a GC internal standard. The liquid/internal standard mixture was also analysed by GC. Both GC analyses indicated that 12.9546 g oligomers were formed of which 12.1773 g (94 mass %) were hexene isomers (99.7% being 1-hexene). Filtration of the liquids gave 0.0143 g of polyethylene.

Example 34

Ethylene Trimerisation Reaction Using CrCl$_3$((2-ethylsulfanyl-ethyl)(3-ethylsulfanyl-propyl)-amine)/MAO The reaction was conducted in a 75 mL stainless steel autoclave equipped with an addition funnel, gas inlet valve and a magnetic stirrer bar. The addition funnel was charged with 0.0039 g (0.0107 mmol) of CrCl3((2-ethylsulfanyl-ethyl)(3-ethylsulfanyl-propyl)-amine) dissolved in 20 mL of toluene and to the base of the autoclave was added 4.3 mL of 1.5M MAO solution in toluene. Over 20 minutes the base of the autoclave was heated to 80° C., after which time the reactor was charged with ethylene to a pressure of 40 bar and the addition funnel was is opened such that the Cr complex solution was allowed to mix with the MAO solution. After 30 minutes at a constant ethylene pressure of 40 bar the reaction was stopped by cooling the autoclave to 0° C. and releasing excess ethylene. The gas released was collected and analysed by GC. The liquid contained in the autoclave was quenched with ethanol followed by 10% hydrochloric acid, and nonane was added as a GC internal standard. The liquid/internal standard mixture was also analysed by GC. Both GC analyses indicated that 4.0487 g oligomers were formed of which 3.2795 g (81 mass %) were hexene isomers (97.9% being 1-hexene). Filtration of the liquids gave 0.0600 g of polyethylene.

TABLE 2

Ethylene trimerisation reactions using CrCl$_3$(bis-(2-decylsulfanyl-ethyl)-amine)/MAO

| Example | CrCl$_3$ complex (mg) | Cr (mmol) | MAO (mmol) | Temp (° C.) | Pressure (barg) | Activity (g prod/ g Cr) | Total product (g) | Solids (Wt %) | Liquids (Wt %) | C$_4$ | C$_6$ | C$_8$ | C$_{10+}$ | 1-Hexene In C$_8$ (Wt %) |
|---|---|---|---|---|---|---|---|---|---|---|---|---|---|---|
| 6 | 15.5 | 0.044 | 29.9 | 100 | 40 | 21767 | 49.80 | 0.58 | 99.00 | 0.3 | 96.0 | 0.5 | 2.5 | 99.4 |
| 7 | 15.5 | 0.044 | 29.9 | 40 | 40 | 2750 | 6.29 | 13.40 | 86.60 | 0.2 | 91.8 | 2.5 | 2.3 | 99.8 |
| 8 | 15.5 | 0.044 | 29.9 | 140 | 40 | 1700 | 3.89 | 19.40 | 80.60 | 0.8 | 94.1 | 0.8 | 1.3 | 99.3 |
| 9¶ | 15.5 | 0.044 | 29.9 | 90 | 40 | 6580 | 15.05 | 7.90 | 92.10 | 0.8 | 95.2 | 1.0 | 1.5 | 99.3 |
| 10 | 15.5 | 0.044 | 29.9 | 100 | 10 | 4424 | 10.12 | 2.49 | 97.51 | 0.8 | 94.2 | 0.7 | 2.8 | 98.6 |
| 11 | 15.5 | 0.044 | 29.9 | 100 | 50 | 23954 | 54.80 | 1.78 | 98.22 | 0.5 | 94.8 | 0.8 | 2.9 | 99.4 |
| 12 | 3.9 | 0.011 | 7.5 | 100 | 40 | 40503 | 23.17 | 0.60 | 99.40 | 0.1 | 98.5 | 0.4 | 0.7 | 99.6 |
| 13 | 15.5 | 0.044 | 9.0 | 100 | 40 | 11500 | 26.31 | 3.07 | 96.93 | 0.1 | 99.2 | 0.4 | 0.5 | 99.5 |
| 14 | 10.6 | 0.030 | 9.0 | 90 | 30 | 32459 | 50.63 | 0.03 | 99.97 | 0.2 | 96.2 | 0.5 | 2.9 | 99.5 |
| 15 | 4.2 | 0.012 | 3.6 | 90 | 30 | 44242 | 27.60 | 0.30 | 99.70 | 0.1 | 97.7 | 0.4 | 1.6 | 99.6 |
| 16 | 10.6 | 0.030 | 3.6 | 90 | 30 | 18116 | 28.26 | 0.76 | 99.24 | 0.1 | 97.8 | 0.4 | 1.5 | 99.6 |
| 17 | 1.4 | 0.004 | 1.1 | 85 | 30 | 96251 | 20.02 | 0.16 | 99.84 | 0.1 | 98.5 | 0.5 | 0.8 | 99.7 |

TABLE 2-continued

Ethylene trimerisation reactions using CrCl₃(bis-(2-decylsulfanyl-ethyl)-amine)/MAO

| Example | CrCl₃ complex (mg) | Cr (mmol) | MAO (mmol) | Temp (° C.) | Pressure (barg) | Activity (g prod/ g Cr) | Total product (g) | Solids (Wt %) | Liquids (Wt %) | Liquid Product Distribution (Wt %) | | | | 1-Hexene In C₈ (Wt %) |
|---|---|---|---|---|---|---|---|---|---|---|---|---|---|---|
| | | | | | | | | | | C₄ | C₆ | C₈ | C₁₀+ | |
| 18 | 4.2 | 0.012 | 2.4 | 85 | 50 | 59312 | 37.01 | 0.10 | 99.90 | 0.1 | 98.0 | 0.7 | 1.1 | 99.7 |
| 19 | 10.6 | 0.030 | 3.6 | 85 | 15 | 23784 | 37.10 | 0.18 | 99.82 | 0.1 | 95.5 | 0.3 | 3.9 | 99.4 |

*Cyclohexane was used as the solvent in this reaction

TABLE 3

Ethylene trimerisation reactions using CrCl₃(bis-(2-decylsulfanyl-ethyl)-amine)/MAO

| Example | CrCl₃ complex (mg) | Cr (mmol) | MAO (mmol) | Temp (° C.) | Pressure (barg) | Activity (g prod/ g Cr) | Total product (g) | Solids (Wt %) | Liquids (Wt %) | Liquid Product Distribution (Wt %) | | | | 1-Hexene In C₈ (Wt %) |
|---|---|---|---|---|---|---|---|---|---|---|---|---|---|---|
| | | | | | | | | | | C₄ | C₆ | C₈ | C₁₀+ | |
| 20 | 13.8 | 0.024 | 14.40 | 90 | 30 | 35250 | 43.99 | 0.21 | 99.79 | 0.4 | 97.5 | 0.4 | 1.3 | 99.4 |
| 21 | 15.0 | 0.026 | 2.60 | 90 | 30 | 38796 | 52.45 | 0.30 | 99.70 | 0.1 | 96.7 | 0.4 | 2.8 | 99.5 |
| 22 | 15.0 | 0.026 | 1.30 | 90 | 45 | 20327 | 27.48 | 2.44 | 97.56 | 0.4 | 94.6 | 0.6 | 3.8 | 99.7 |
| 23 | 6.9 | 0.012 | 1.20 | 100 | 45 | 71018 | 44.31 | 0.30 | 99.70 | 0.2 | 97.5 | 0.6 | 1.5 | 99.7 |
| 24 | 6.9 | 0.012 | 0.60 | 90 | 47 | 31700 | 19.78 | 1.05 | 98.95 | 0.2 | 96.6 | 0.5 | 1.4 | 99.7 |
| 25 | 4.6 | 0.008 | 0.40 | 90 | 45 | 44000 | 18.30 | 0.67 | 99.33 | 0.1 | 98.7 | 0.8 | 0.4 | 99.7 |
| 26 | 6.9 | 0.012 | 0.36 | 90 | 45 | 46350 | 26.92 | 2.37 | 97.63 | 0.1 | 98.4 | 0.6 | 0.9 | 99.7 |
| 27 | 6.9 | 0.012 | 0.36 | 90 | 45 | 37650 | 23.49 | 0.49 | 99.51 | 0.1 | 97.9 | 0.6 | 1.3 | 99.7 |

The invention claimed is:

1. A catalyst system for the oligomerisation of olefins, the system comprising a mixed heteroatomic ligand, which ligand includes at least three heteroatoms of which at least one is sulfur and at least 2 heteroatoms are not the same, and a chromium, wherein none of the non-carbon based heteroatoms in the ligand is directly bonded to any of the other non-carbon based heteroatoms and the ligand is selected from the following ligand types:

(a) $R^1A(R^2BR^3)(R^4CR^5)$ wherein $R^1$, $R^3$ and $R^5$ may be hydrogen or be independently selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^4$ may be the same or different and are $C_1$ to $C_{15}$ hydrocarbyls; A is nitrogen or phosphorous; and B and C are sulfur; and (b) $R^1A(R^2BR^3R^4)(R^5CR^6)$ wherein $R^1$, $R^3$, $R^4$, and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^5$ may be the same or different and are $C_1$ to about $C_{15}$ hydrocarbyls; A and B are independently nitrogen or phosphorous; and C is sulfur; and (c) $A(R^1BR^2R^3)(R^4CR^5)$ wherein $R^2$, $R^3$, and $R^5$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B is nitrogen or phosphorous; and A and C are sulfur; and (d) $A(R^1BR^2R^3)(R^4CR^5R^6)$ wherein $R^2$, $R^3$, $R^5$ and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B and C are independently nitrogen or phosphorous; and A is sulfur.

2. A catalyst system of claim 1, wherein the ligand is a multidentate mixed heteroatomic ligand.

3. A catalyst system as claimed in claim 2, wherein the ligand contains, in addition to sulfur, at least one nitrogen or phosphorous heteroatom.

4. A catalyst system as claimed in claim 2, wherein the ligand is selected from bis-(2-ethylsulfanyl-ethyl)-amine, bis-(2-methylsulfanyl-ethyl)-amine, bis-(2-butylsulfanyl-ethyl)-amine, bis-(2-decylsulfanyl-ethyl)-amine, bis-(ethylsulfanyl-methyl)-amine, bis-(2-ethylsulfanyl-phenyl)-amine, bis-(2-ethylsulfanyl-ethyl)-phosphine, bis-(2-ethylsulfanyl-ethyl)-ethylphosphine, bis-(2-ethylsulfanyl-ethyl)-phenylphosphine, N-methylbis-(2-ethylsulfanyl-ethyl)-amine, (2-ethylsulfanyl-ethyl)(3-ethylsulfanyl-propyl)-amine, (2-ethylsulfanyl-ethyl)(2-diethylphosphino-ethyl)amine, (2-ethylsulfanyl-ethyl)(2-diethylphosphino-ethyl)-sulfide (2-ethylsulfanyl-ethyl)(2-diethylamino-ethyl)-amine and (2-ethylsulfanyl-ethyl)(2-diethylamino-ethyl)sulfide, (2-ethylsulfanyl-ethyl)(2-diethylphosphino-ethyl)phosphine,(2-ethylsulfanyl-ethyl)(2-diethylamino-ethyl)-ethylphosphine, bis-(2-diethylphosphino-ethyl)-sulfide, bis-(2-diethylamino-ethyl)sulfide, (2-diethylphosphino-ethyl)(2-diethylamino-ethyl)sulfide and derivatives thereof.

5. A catalyst system as claimed in claim 1, wherein the oligomerisation catalyst system is a trimerisation of α-olefins catalyst system.

6. A catalyst system as claimed in claim 1, wherein the oligomerisation catalyst system is a trimerisation of ethylene to 1-hexene catalyst system.

7. A catalyst system as claimed in claim 1, the system further comprising an aluminoxane.

8. A catalyst system as claimed in claim 7, wherein the aluminoxane forms part of a mixture of aluminoxanes.

9. A catalyst system as claimed in claim 8, wherein the chromium coordination complex is expressed by the formula $LCrX_n$, wherein X represents anions which can be the same or different, n is an integer from 0 to 5 and L is a mixed heteroatomic ligand.

10. A catalyst system as claimed in claim 7, wherein the chromium source for the preparation of the coordination complex is selected from an organic or inorganic chromium compound, with the oxidation state of the chromium atom ranging from 0 to 6.

11. A catalyst system as claimed in claim 7, wherein a chromium salt is used in the preparation of the catalyst system and the chromium salt is selected from chromium (III)acetylacetonate, chromium (III) acetate, chromium (III) 2,2,6,6-tetramethylheptadionate, chromium (III) tris(2-ethylhexanoate, chromium (III) chloride, chromium (II) acetate, chromium (II) chloride, chromium (II) nitrate and chromium (III) sulphate.

12. A catalyst system as claimed in claim 7, wherein the aluminoxane is prepared from a trialkylaluminium.

13. A catalyst system as claimed in claim 7, the system further comprising a trialkylaluminium.

* * * * *